United States Patent [19]

Ito et al.

[11] Patent Number: 4,705,813

[45] Date of Patent: Nov. 10, 1987

[54] PROCESS FOR PRODUCING POROUS FILMS INVOLVING A STRETCHING STEP AND THE RESULTANT FILM

[75] Inventors: Keiko Ito, Nakatsugawa; Michiyasu Ito, Kuwana; Shoichi Tsuji, Nagoya; Hisatosi Suzuki, Okazaki; Shoichi Ito, Nagoya, all of Japan

[73] Assignee: Mitsui Toatsu Chemicals, Inc., Japan

[21] Appl. No.: 681,946

[22] Filed: Dec. 14, 1984

[30] Foreign Application Priority Data

Dec. 16, 1983 [JP] Japan ................................. 58-236333

[51] Int. Cl.$^4$ ....................... B29C 67/20; B29C 55/10
[52] U.S. Cl. ........................................ 521/92; 264/41; 264/147; 264/154; 264/288.8; 264/290.2; 264/DIG. 13; 521/134; 521/143; 521/144; 521/149
[58] Field of Search ......... 264/41, 147, 154, DIG. 13, 264/288.8, 290.2; 521/92, 134, 143, 144, 149

[56] References Cited

U.S. PATENT DOCUMENTS 3,783,088 1/1974 Yoshiyasu et al. .
4,472,328 9/1984 Sugimoto et al. .............. 264/147 X

OTHER PUBLICATIONS

*The Encyclopedia of Patent Practice and Invention Management* Robert Calvert, Edt., New York, Reinhold, 1964, pp. 151–153.

*Primary Examiner*—Philip Anderson
*Attorney, Agent, or Firm*—McGlew and Tuttle

[57] ABSTRACT

A process for producing porous films which comprises blending 100 parts by weight of a polyolefin resin with 50 to 500 parts by weight of barium sulfate preferably having an average particle diameter of 0.1 to 7 μm, melting the resulting resin composition and forming it into a film, and then stretching the film at least uniaxially by a factor of 1.5 to 7.

6 Claims, No Drawings

PROCESS FOR PRODUCING POROUS FILMS INVOLVING A STRETCHING STEP AND THE RESULTANT FILM

BACKGROUND OF THE INVENTION (a) Field of the Invention:

This invention relates to an improved process for producing porous films. More particularly, it relates to a process for producing porous films which comprises blending a polyolefin resin with barium sulfate as a filler, melting the resulting resin composition and forming it into a film, and then stretching the film at least uniaxially.

(b) Description of the Prior Art:

Conventionally, there are a large number of well-known processes for producing porous films by forming a resin composition comprising a polyolefin resin and any of various noncompatible fillers into a film and then stretching this film. For example, Japanese Patent Laid-Open Nos. 47334/'82 and 203520/'82 disclose a process for producing porous films which comprises melting a resin composition obtained by blending a polyolefin resin with a filler and liquid rubber or a hydroxylated poly-saturated-hydrocarbon, forming the molten resin composition into a sheet or film, and then stretching this sheet or film. Moreover, Japanese Patent Laid-Open No. 15538/'83 discloses a process for producing porous films which comprises melting a resin composition obtained by blending a linear low-density polyethylene resin with a filler and a liquid or waxy hydrocarbon polymer, forming the molten resin composition into a sheet or film, and then stretching this sheet or film. However, the films produced by these processes are disadvantageous in that they exhibit surface tackiness due to the aforesaid component contained in addition to the polyolefin resin and the filler and in that they can only be practically used in relatively large thickness because of their low mechanical strength.

Furthermore, it is described in Japanese Patent Laid-Open No. 149303/'83 that such porous films can be used as a leakproof sheet in disposable diapers. Porous films for use as the leakproof sheet of a disposable diaper are produced by blending 100 parts by weight of a polyolefin resin with 28 to 200 parts by weight of a filler and 10 to 70 parts by weight of a liquid or waxy hydrocarbon polymer, forming the resulting resin composition into a film, and then stretching this film at least uniaxially by a factor of 1.2 or greater. However, this process for producing porous films has the disadvantages that some types of fillers give poor stretchability and hence fail to provide fully uniform pores and that the resulting film tends to produce a disagreeable noise. Moreover, the concurrent use of a hydrocarbon polymer makes this process unsatisfactory because the hydrocarbon polymer tends to bloom to the film surface and causes a sticky sensation.

Such porous films are also useful as a leakproof sheet in sanitary napkins. Conventionally, a sheet of paper which has been rendered liquidimpermeable by means of a synthetic resin such as polyethylene has been used for this purpose. However, the resulting sanitary napkins have the disadvantage of causing a disagreeable sensation during prolonged use because of their lack of permeability to water vapor.

SUMMARY OF THE INVENTION

Accordingly, it is an object of the present invention to provide an improved process for producing porous films.

It is another object of the present invention to provide a process for producing porous films which have sufficient high porosity and thereby exhibit high moisture permeability and gas permeability while retaining excellent water resistance.

It is still another object of the present invention to provide a process for producing porous films which are free from surface tackiness, have excellent softness and show little reduction in strength.

It is a further object of the present invention to provide an improved leakproof sheet for use in disposable diapers.

It is a further object of the present invention to provide an improved leakproof sheet for use in sanitary napkins.

Other objects of the present invention will be apparent from the following description.

According to the present invention, there is provided a process for producing porous films which comprises melting a resin composition consisting essentially of 100 parts by weight of a polyolefin resin and 50 to 500 parts by weight of barium sulfate, forming the molten resin composition into a film, and then stretching the film at least uniaxially by a factor of 1.5 to 7.

The expression "a resin composition consisting essentially of 100 parts by weight of a polyolefin resin and 50 to 500 parts by weight of barium sulfate" as used herein means that the resin composition may further contain (1) at least one additive selected from common stabilizers, antioxidants, colorants, ultraviolet light absorbents and hydrocarbon-free lubricants and/or (2), in addition to the barium sulfate, other inorganic fillers (such as calcium carbonate and the like) or common inorganic and organic modifiers in an amount less than that of barium sulfate used (for example, not greater than 20% based on the amount of barium sulfate used), but the addition of liquid rubber, a hydroxylated poly-saturated-hydrocarbon or a hydrocarbon polymer as described in the aforementioned Japanese Patent Laid-Open Nos. 47334/'82, 203520/'82, 15538/'83 and 149303/'83 should be positively avoided in order to obtain a porous film free from surface tackiness.

According to the present invention, porous films which are free from surface tackiness and have excellent properties and which have been unobtainable in the prior art can be produced without using any of the above-described additives used in the prior art. This can be accomplished simply by specifying the type of the filler, its amount used and preferably its average particle diameter, using a polyolefin resin, and stretching the film by a specific factor.

DETAILED DESCRIPTION OF THE INVENTION

The polyolefin resins which can be used in the present invention include homopolymers such as polypropylene, low-density polyethylene, high-density polyethylene, linear low-density polyethylene, polybutylene, etc.; copolymers such as ethylenepropylene copolymer, ethylene-butylene copolymer, ethylene-vinyl acetate copolymer, etc.; and blends thereof.

In the practice of the present invention, it is preferable to use barium sulfate having an average particle diameter of 0.1 to 7 μm and more preferably 0.5 to 5 μm. If the average particle diameter is smaller than 0.1 μm, well-defined pores cannot be obtained. On the contrary, if it is larger than 7 μm, the resulting film will have poor stretchability and, therefore, well-defined pores can hardly be obtained just as in cases where the average particle diameter is too small.

The barium sulfate is used in an amount of 50 to 500 parts by weight, and preferably 100 to 400 parts by weight, per 100 parts by weight of the polyolefin resin. If the amount of barium sulfate used is less than 50 parts by weight, sufficiently high porosity cannot be obtained, while if it is greater than 500 parts by weight, the resulting film cannot be fully stretched because of its increased rigidity and, therefore, will show a reduction in porosity.

It is preferable to subject the barium sulfate to surface treatment with a fatty acid or a metallic salt thereof, silicone, silane, a resin acid or the like, because this treatment is effective in improving its dispersibility in the resin and producing well-defined pores.

So far as the effects of the present invention are not impaired, other inorganic fillers such as calcium carbonate and the like or common inorganic and organic modifiers may be used in addition to the barium sulfate. However, these additives should be used in an amount of not greater than 20% based on the amount of barium sulfate used.

Now, the present process for producing porous films will be specifically described hereinbelow.

According to the need, at least one additive selected from stabilizers, antioxidants, colorants, ultraviolet light absorbents and lubricants is added to a polyolefin resin and barium sulfate. These ingredients are mixed with a Henschel mixer, supermixer or tumbling mixer. Thereafter, using an ordinary single-screw or twin-screw extruder, the resulting mixture is blended and pelletized. Then, using an inflation extruder or T-die extruder, these pellets (alone or in admixture with polyolefin resin pellets) are melted at a temperature higher than the melting point of the polyolefin resin (preferably, by 20° C. or more) and lower than the decomposition temperature thereof, and formed into a film. In some cases, the aforesaid mixture may be directly formed into a film with an extruder, instead of being pelletized. Subsequently, the film is at least uniaxially stretched by a factor of 1.5 to 7 according to a conventional technique such as roll stretching, tentering or the like. This stretching may be performed in steps and/or in two or more directions. In the case of biaxial stretching, however, it is preferable to stretch the film simultaneously in the two directions. In order to enhance the morphological stability of pores, the stretched film may be annealed by heating.

In a particularly preferred embodiment, a thin, uniform porous film having a thickness of 40 μm or less can be produced by blending 100 parts by weight of a polyolefin resin with 100 to 200 parts by weight of barium sulfate having an even distribution of particle diameters ranging from 0.5 to 1 μm, melting the resulting resin composition and forming it into a film, and then stretching the film at least uniaxially by a factor of 0.5 to 7.

The porosity is determined by the amount of barium sulfate used, the stretching factor and the like. If the stretching factor is less than 1.5, sufficiently high porosity cannot be obtained, while if it is greater than 7, a porous film cannot be steadily produced because of its frequent breakage during the stretching process.

Porous films produced by the process of the present invention are characterized by high porosity, excellent softness and little reduction in strength.

Moreover, since the good affinity between the polyolefin resin and barium sulfate provides good stretchability, not only good workability but also an even distribution of pores can be achieved and, therefore, a porous film can be produced steadily.

Thus, the porous films of the present invention have sufficient high porosity and hence exhibit good moisture permeability and gas permeability while retaining excellent water resistance, so that they can be used in clothing and sanitary applications. In addition, they can also be used as a filtering medium owing to their even distribution of pores.

The present invention is further illustrated by the following examples. However, these examples are given for purposes of illustration only and are not to be construed to limit the scope of the invention.

In the examples, melt index (MI) was determined according to ASTM D-1238 and density was determined according to ASTM D-1505.

Also in the examples, film properties were evaluated according to the following procedures:

(1) Strength

Using a Tensilon tensile testing machine, a piece of film measuring 25 mm (wide) x 100 mm (long) is tested at a straining rate of 200 mm/min. Its strength at breakage is determined with respect to the machine direction (MD) and the transverse direction (TD).

(2) Moisture permeability

Moisture permeability is tested according to ASTM E96(D).

(3) Softness

Softness is evaluated by the feel and rated according to the following criteria:

A=very soft and smooth.
B=Rather soft and smooth.
C=Hard and rough.

EXAMPLES 1-11 AND COMPARATIVE EXAMPLES 1-5

Each of the fillers given in Table 1 was added to the corresponding base resin in the amount given in Table 1, and mixed therewith by means of a Henschel mixer. Thereafter, using a twin-screw extruder, the resulting mixture was intimately blended and formed into pellets. Then, using a T-die extruder, these pellets were melted at a temperature 80° C. higher than the melting point of the base resin and formed into a film. This film was uniaxially or biaxially (Example 3) stretched by the factor given in Table 1 to obtain a porous film having the thickness given in Table 1. However, the film was not stretched in Comparative Example 1 and could not be stretched into a porous film in Comparative Example 2. In Comparative Example 5, the film could only be stretched by a factor of up to 2. In Comparative Example 3, no sampling was possible because of frequent breakage during the stretching process.

The strength, moisture permeability and softness of the porous films thus obtained were evaluated according to the above-described procedures and the results are shown in Table 1.

TABLE 1

| | Base resin Type[1] | Base resin Trade name (manufacturer) | Filler Type | Filler Average particle diameter (μm) | Filler Amount[2] (phr) | Stretching factor | Film thickness (μm) | Strength (kg/25 mm) MD | Strength (kg/25 mm) TD | Moisture permeability (g/m²/24 hr) | Softness |
|---|---|---|---|---|---|---|---|---|---|---|---|
| Example | | | | | | | | | | | |
| 1 | LDPE | REXLON F-41 (Nippon Petrochemicals Co., Ltd.) | BaSO₄ | 0.8 | 150 | 4 | 40 | 6.0 | 1.5 | 3,500 | A |
| 2 | " | REXLON F-41 (Nippon Petrochemicals Co., Ltd.) | " | " | " | 5 | " | 6.5 | 1.3 | 4,200 | A |
| 3 | " | REXLON F-41 (Nippon Petrochemicals Co., Ltd.) | " | " | " | 2 × 2 | " | 4.9 | 4.5 | 3,900 | A |
| 4 | L-LDPE | NUCG-5511 (Nippon Unicar Co., Ltd.) | " | 4.2 | 50 | 6 | " | 7.5 | 1.3 | 2,500 | A |
| 5 | " | NUCG-5511 (Nippon Unicar Co., Ltd.) | " | 0.8 | 150 | 4 | " | 6.2 | 1.6 | 6,500 | A |
| 6 | " | NUCG-5511 (Nippon Unicar Co., Ltd.) | " | 0.5 | 100 | 7[3] | 20 | 9.0 | 0.7 | 7,000 | A |
| 7 | " | NUCG-5511 (Nippon Unicar Co., Ltd.) | " | " | 300 | 2.5 | 40 | 5.0 | 1.3 | 4,500 | A |
| 8 | " | NUCG-5511 (Nippon Unicar Co., Ltd.) | " | " | 500 | 1.5 | " | 5.8 | " | 4,000 | A |
| 9 | HDPE | Hi-zex HZ5000S (Mitsui Petrochemical Industries, Inc.) | " | 0.8 | 150 | 5 | " | 8.0 | 2.2 | 4,500 | C |
| 10 | PP | MITSUI NOBLEN JS-G (Mitsui Toatsu Chemicals, Inc.) | " | " | " | " | " | 10.3 | 2.5 | 4,900 | C |
| 11 | EPC | MITSUI NOBLEN MJS-G (Mitsui Toatsu Chemicals, Inc.) | " | " | " | " | " | 9.1 | 2.3 | 4,000 | C |
| Comparative Example | | | | | | | | | | | |
| 1 | L-LDPE | NUCG-5511 (Nippon Unicar Co., Ltd.) | " | " | " | Unstretched | 50 | 2.3 | 2.2 | 15 | A |
| 2 | " | NUCG-5511 (Nippon Unicar Co., Ltd.) | " | " | 600 | Unstretched | — | — | — | — | — |
| 3 | " | NUCG-5511 (Nippon Unicar Co., Ltd.) | " | " | 150 | 10[4] | — | — | — | — | — |
| 4 | " | NUCG-5511 (Nippon Unicar Co., Ltd.) | CaCO₃ | 1.0 | " | 4 | 70 | 4.3 | 0.8 | 3,000 | C |
| 5 | " | NUCG-5511 (Nippon Unicar Co., Ltd.) | Glass beads | 1.2 | 120 | 2 | 50 | 1.5 | 0.7 | 30 | C |

Notes:
[1]LDPE = low-density polyethylene.
L-LDPE = linear low-density polyethylene.
PP = polypropylene.
HDPE = high-density polyethylene.
EPC = ethylene-propylene copolymer.
[2]Parts by weight of the filler per 100 parts by weight of the base resin.
[3]The maximum value at which stretching could be performed steadily.
[4]No sampling was possible because of frequent breakage during the stretching process.

Porous films produced by the process of the present invention have high porosity and excellent softness and, moreover, show little reduction in strength, so that they are very suitable for use as a leakproof sheet in disposable diapers. Although such a leakproof sheet is generally used as the outermost layer of a disposable diaper, a material (such as a common punched film or sterically embossed sheet) not impairing its moisture permeability may be superposed on the outer side of the leakproof sheet to impart a cloth-like appearance thereto.

In such disposable diapers, there may be used any of the common liquid absorbers including fluff composed of pulp fibers, such fluff wrapped in absorbent paper or the like, polymeric absorbers having high water absorbency, and the like.

As the liquid-permeable sheet which will be in direct contact with the skin, there may preferably be used a non-woven fabric composed of polyester fibers, nylon fibers, polyolefin fibers or the like.

In addition, there may be used pressure-sensitive tapes for fastening the diaper, and elastic members (such as rubber members) provided along the side edges to prevent leakage.

Disposable diapers are made by placing a liquid absorber on the aforesaid leakproof sheet, and stacking a liquid-permeable sheet thereon.

In disposable diapers using the porous film of the present invention as the leakproof sheet, the outermost leakproof sheet has a large number of pores. Since these pores allow water vapor to pass therethrough while retaining water droplets, the skin of the infant is not dampened but kept in a dry state, resulting in little tendency to develop diaper rash. Moreover, they also have the advantages of being hardly torn because of their high strength and being soft enough to produce no disagreeable noise.

The following example illustrates the use of the porous film of the present invention as a leakproof sheet in disposable diapers.

EXAMPLE 12

Disposable diapers were made by placing a filling of fluffy pulp and a non-woven polyester fabric on each of the porous films obtained in Examples 1-11, and then providing it with pressure-sensitive tapes and rubber members.

These disposable diapers were superior in the softness of the leakproof sheet to those of the comparative examples given hereinbelow, so that they produced no disagreeable noise during use and felt comfortable to the touch. When these disposable diapers were tested by using them practically on infants, they caused no rash on the skin of the wearer.

COMPARATIVE EXAMPLE 6

Using the porous films obtained in Comparative Examples 1, 4 and 5, disposable diapers were made in the same manner as described in Example 12.

These disposable diapers were inferior in the softness of the leakproof sheet to those of Example 12, so that they felt uncomfortable to the touch and produced a disagreeable noise. When these disposable diapers were tested by using them practically on infants, they caused an extensive rash or at least a slight rash (in the case of the film of Comparative Example 4).

COMPARATIVE EXAMPLE 7

120 parts by weight of calcium carbonate having an average particle diameter of 1.2 $\mu$m and 20 parts by weight of liquid polybutadiene (Nisso PBG; Nippon Soda Co., Ltd.) or rubbery EPR (Toughmer P0480; Mitsui Petrochemical Industries, Inc.) were added to 100 parts by weight of linear low-density polyethylene (L-LDPE) having a melt index (MI) of 5, and mixed therewith by means of a Henschel mixer. Thereafter, using a twin-screw extruder, the resulting mixture was intimately blended and formed into pellets. Then, using a 40 mm$\phi$ inflation extruder, these pellets were formed into a film. This film was roll stretched at 80° C. by a factor of 3.0 to obtain a porous film having a thickness of 50 $\mu$m. This porous film varied in moisture permeability according to the location and exhibited a slight degree of surface tackiness. Disposable diapers using this porous film as the leakproof sheet caused a slight rash on the skin of infants.

Porous films obtained by the process of the present invention have high porosity and excellent softness and, moreover, show little reduction in strength in spite of their small thickness, so that they are very suitable also for use as a leakproof sheet in sanitary napkins. Conventional sanitary napkins are so constructed that a liquid absorber such as fluffy pulp, cotton, absorbent resin or the like is partially covered with a film of paper having been rendered liquid-impermeable by treatment with a synthetic resin such as polyethylene or the like and the resulting structure is then wrapped in a non-woven woven fabric. In sanitary napkins using the porous film of the present invention as the leakproof sheet, this leakproof sheet has a large number of pores which allow water vapor to pass therethough. Accordingly, they can keep the skin of the user in a dry state and cause no disagreeable sensation even during prolonged use.

The following example illustrates the use of the porous film of the present invention as a leakproof sheet in sanitary napkins.

EXAMPLE 13

Sanitary napkins were made by covering a filling of fluffy pulp partially with each of the porous films obtained in Examples 1-11, wrapping the resulting structure in a non-woven fabric and then heat sealing its overlapping portions. When these sanitary napkins and commercially available ones having a liquid-impermeable film of polyethylene-coated paper were comparatively tested by using them practically for prolonged periods of time, the sanitary napkins in accordance with the present invention did not cause a disagreeable, stuffy sensation.

What is claimed is:

1. A process for producing porous films which comprises the steps of:
   (a) melting a resin composition consisting essentially of a polyolefin resin selected from the group consisting of polypropylene, high-density polyethylene, ethylene-propylene copolymer, polybutylene, ethylene-butylene copolymer, ethylene vinyl acetate copolymer, and blends thereof, or a blend of the polyolefin resin with low-density polyethylene of linear low-density polyethylene, with or without a hydrocarbon-free lubricant, and a filler that is non-compatible with said polyolefin resin and in an amount of 50 to 500 parts by weight per 100 parts by weight of said plyolefin resin, said filler being $BaSO_4$ with an average particle diameter of from 0.1 to 7 $\mu$m, said melting step being carried out at a temperature higher than the melting point of said polyolefin resin, but lower than the decomposition temperature thereof;
   (b) forming the thus melted resin composition into a film; and
   (c) stretching the thus formed film at least uniaxially by a factor of 1.5 to 7.

2. A process as claimed in claim 1 wherein the average particle diameter of the barium sulfate is in the range of 0.5 to 5 $\mu$m.

3. A process as claimed in claim 1 wherein the barium sulfate is added in an amount of 100 to 400 parts by weight per 100 parts by weight of the polyolefin resin.

4. A process as claimed in claim 1 wherein the barium sulfate has been subjected to surface treatment with a fatty acid or a metallic salt thereof, silicone, silane or a resin acid.

5. A porous film having water resistance, mositure permeability and gas permeability which is produced by a process as claimed in any one of claims 1, 2, 3, and 4.

6. The porous film according to claim 5, wherein said film is fluid-impermeable sheet for diapers or sanitary napkins.

* * * * *

UNITED STATES PATENT OFFICE
CERTIFICATE OF CORRECTION

Patent No. 4,705,813     Dated November 10, 1987

Inventor(s) Ito et al

It is certified that error appears in the above-identified patent and that said Letters Patent are hereby corrected as shown below:

Claim 1, line 47 in Column 8 of issued patent "of" should be --or--.

Signed and Sealed this

Twenty-sixth Day of July, 1988

*Attest:*

DONALD J. QUIGG

*Attesting Officer*     *Commissioner of Patents and Trademarks*